US008551106B2

(12) United States Patent
Harrold

(10) Patent No.: US 8,551,106 B2
(45) Date of Patent: Oct. 8, 2013

(54) METHOD AND APPARATUS FOR INSTALLATION OF INTRAMEDULLARY MEDICAL DEVICE

(75) Inventor: Mark Harrold, Foothill Ranch, CA (US)

(73) Assignee: Arthrocare Corporation, Austin, TX (US)

(*) Notice: Subject to any disclaimer, the term of this patent is extended or adjusted under 35 U.S.C. 154(b) by 166 days.

(21) Appl. No.: 13/250,890

(22) Filed: Sep. 30, 2011

(65) Prior Publication Data

US 2013/0085502 A1    Apr. 4, 2013

(51) Int. Cl.
*A61B 17/58*    (2006.01)
*A61B 17/60*    (2006.01)
*A61F 2/00*    (2006.01)

(52) U.S. Cl.
USPC .............................. 606/96; 606/62; 606/104

(58) Field of Classification Search
USPC .................. 606/62–64, 86 R, 96–99, 104
See application file for complete search history.

(56) References Cited

U.S. PATENT DOCUMENTS

| | | | | |
|---|---|---|---|---|
| 4,667,664 A | * | 5/1987 | Taylor et al. | 606/64 |
| 4,865,025 A | * | 9/1989 | Buzzi et al. | 606/96 |
| 4,889,111 A | * | 12/1989 | Ben-Dov | 606/56 |
| 4,913,137 A | * | 4/1990 | Azer et al. | 606/64 |
| 5,034,013 A | | 7/1991 | Kyle et al. | |
| 5,505,734 A | | 4/1996 | Caniggia et al. | |
| D379,855 S | | 6/1997 | Perry | |
| 5,658,287 A | | 8/1997 | Hofmann et al. | |
| 5,766,174 A | | 6/1998 | Perry | |
| 5,855,579 A | | 1/1999 | James et al. | |
| 5,976,138 A | | 11/1999 | Baumgart et al. | |
| 6,093,192 A | * | 7/2000 | Abel | 606/98 |
| 6,123,708 A | | 9/2000 | Kilpela et al. | |
| 6,168,595 B1 | | 1/2001 | Durham et al. | |
| 6,200,317 B1 | | 3/2001 | Aalsma et al. | |
| 6,261,290 B1 | | 7/2001 | Friedl | |
| 6,488,684 B2 | | 12/2002 | Bramlet et al. | |
| 6,579,293 B1 | | 6/2003 | Chandran | |
| 6,808,527 B2 | | 10/2004 | Lower et al. | |
| 6,921,400 B2 | | 7/2005 | Sohngen | |
| 7,056,322 B2 | | 6/2006 | Davison et al. | |
| D604,846 S | | 11/2009 | Hintermann | |

(Continued)

FOREIGN PATENT DOCUMENTS

WO    WO 95/24870    9/1995
WO    WO 2005/094705    10/2005

OTHER PUBLICATIONS

Ankle Arthrodesis Nail Surgical Technique, pp. 1-16, BioMet, Inc., Warsaw, Indiana, USA, 2000.

(Continued)

*Primary Examiner* — Andrew Yang
(74) *Attorney, Agent, or Firm* — Greenberg Traurig, LLP

(57) ABSTRACT

Methods and apparatus for installing intramedullary medical devices (e.g., intramedullary nails) are described herein. Intramedullary medical devices in accordance with this disclosure provide sustained compressive forces across a bone fusion site despite bone resorption processes. Intramedullary medical devices in accordance with this disclosure include pseudo-elastic shape memory alloys containing nickel and titanium. Portions of intramedullary medical devices, including shape memory alloy elements in the intramedullary medical devices, may have strains imparted upon them through the methods and apparatus described herein. Further aspects of surgery techniques are also performed and controlled through the methods and apparatus described herein.

22 Claims, 6 Drawing Sheets

(56) References Cited

U.S. PATENT DOCUMENTS

| | | | |
|---|---|---|---|
| 8,231,629 B2* | 7/2012 | Lerner et al. | 606/87 |
| 2002/0058949 A1* | 5/2002 | Iaia | 606/98 |
| 2004/0230193 A1 | 11/2004 | Cheung et al. | |
| 2005/0096656 A1* | 5/2005 | Behrens | 606/64 |
| 2005/0107791 A1 | 5/2005 | Manderson | |
| 2005/0159749 A1 | 7/2005 | Levy et al. | |
| 2006/0064106 A1* | 3/2006 | Fernandez | 606/98 |
| 2006/0264945 A1 | 11/2006 | Edidin et al. | |
| 2007/0100342 A1* | 5/2007 | Green et al. | 606/64 |
| 2008/0287949 A1 | 11/2008 | Keith et al. | |
| 2008/0300597 A1 | 12/2008 | Morgan et al. | |
| 2009/0149861 A1 | 6/2009 | Brodsky et al. | |

OTHER PUBLICATIONS

Panta Ankle Arthrodesis Nail Surgical Technique brochure, pp. 1-23, Integra Lifesciences Corporation, Plainsboro, New Jersey.

Retro Nail Ankle Arthrodesis treats arthritic deformity, factures, failed fusion, retrieved from the Internet Apr. 4, 2007 at http;//www.orthofix.com/products/retronail.asp?cid=5, ©2007 orthofix.com.

T2 Tibial Nailing System, Operative Technique, pp, 1-31, Stryker Trauma GmbH, Germany, 2004.

Tibiotalocalcaneal Fusion Using the Versa Nail™, Surgical Technique, pp. 1-15, DePuy Orthopaedics, Inc., Warsaw, Indiana, USA, 2002.

Versanail TTC, Surgical Technique Tibiotalocalcanea Nailing System Options Made Easy, pp. 1-19, Trauma & Extremities Group, DePuy, a Johnson & Johnson Company, 2006.

* cited by examiner

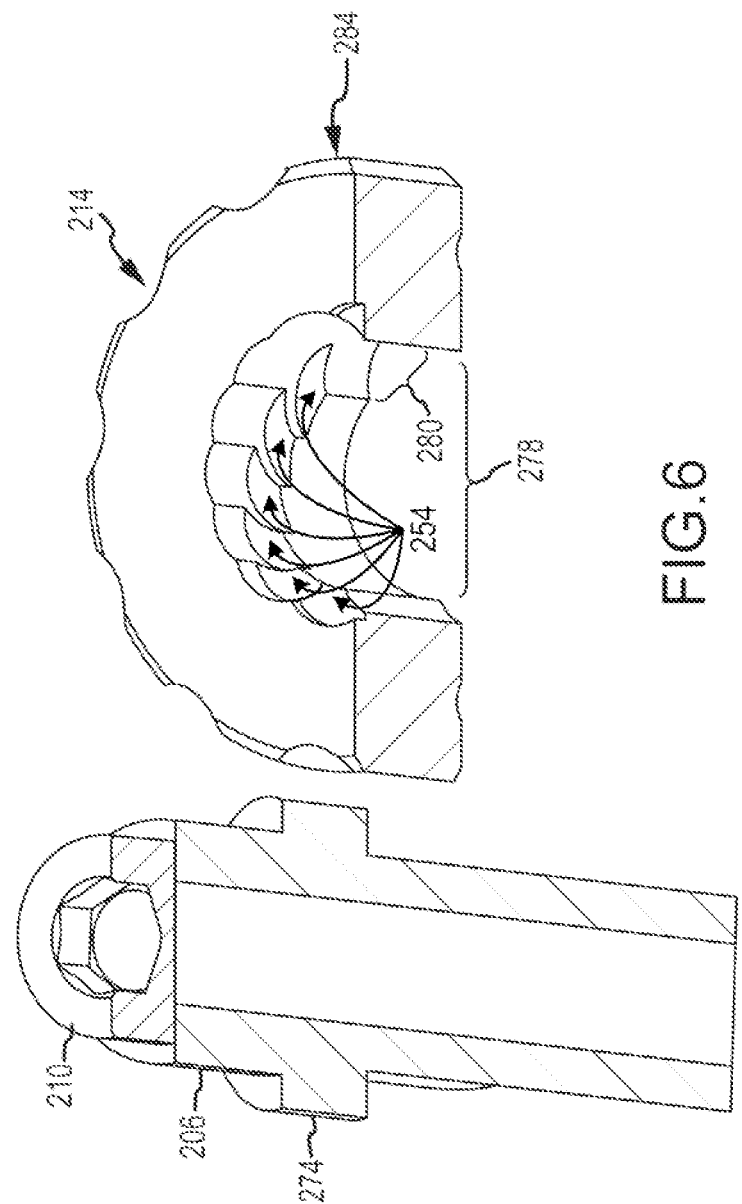

METHOD AND APPARATUS FOR INSTALLATION OF INTRAMEDULLARY MEDICAL DEVICE

BACKGROUND

Intramedullary medical devices provide stability and/or compression during bone fusion processes. Tibio-talo-calcaneal ankle fusion (TTC) procedure is a technique which may be used in order to achieve functional, stable, and pain-free orthopedic fusion for the treatment of appropriate medical conditions. Intentional bone fusions which are unsuccessful can lead to patient pain, recurring surgery, infection, loss of limb function, and/or, in extreme cases, limb amputation. Surgery to install a device for TTC ankle fusion is a procedure involving specific tolerances and exacting standards. Methods and apparatus for installing intramedullary devices can aid physicians in installing intramedullary devices correctly and efficiently, and can reduce the incidence of error.

SUMMARY

Methods and apparatus for installing intramedullary medical devices (e.g., intramedullary nails) are described herein. Intramedullary medical devices in accordance with this disclosure provide sustained compressive forces across a bone fusion site despite bone resorption processes. Intramedullary medical devices in accordance with this disclosure include pseudo-elastic shape memory alloys containing nickel and titanium. Portions of intramedullary medical devices, including shape memory alloy elements in the intramedullary medical devices, may have strains imparted upon them through the methods and apparatus described herein. Further aspects of surgery techniques are also performed and controlled through the methods and apparatus described herein.

In one aspect, the disclosure describes an installation assembly for installing an intramedullary medical device into a patient. In one embodiment, the installation assembly includes a distal drill guide holder carriage connecting a first distal drill guide holder to a second distal drill guide holder, wherein the distal drill guide holder carriage is further connected to a distal anchor element lock adapted to attach the distal drill guide holder carriage to a distal anchor element of an intramedullary medical device having a central axis. The distal drill guide holder carriage is further adapted to translate both the first and second distal drill guide holders parallel to the central axis of the intramedullary medical device and registered to a first position along the central axis that includes the distal anchor element. The installation assembly further includes a proximal drill guide holder carriage connecting a first proximal drill guide holder to a second proximal drill guide holder, the proximal drill guide holder carriage slideably connected with the distal drill guide holder carriage through a compression assembly adapted to translate the distal anchor element lock along the central axis, from an initial position with respect to a proximal anchor element of the intramedullary medical device. The proximal drill guide holder carriage is further adapted to translate both the first and second proximal drill guide holders parallel to the central axis of the intramedullary medical device and registered to a second position along the central axis that includes the proximal anchor element. The installation assembly further includes an initial compression stop of the compression assembly adapted to limit the compression assembly from distally translating the distal anchor element lock past a predetermined maximum compression distance along the central axis from the initial position and a strain release stop adapted to limit the compression assembly, once the distal anchor element has been distally translated at least to a predetermined minimum installed distance, from proximally translating the distal anchor element to less than a selectable installed distance. The installation assembly further includes a supra-proximal drill guide holder carriage connecting a first supra-proximal drill guide holder to a second supra-proximal drill guide holder, the supra-proximal drill guide holder carriage slideably connected with the proximal drill guide holder carriage through a joint-compression assembly adapted to translate the proximal drill guide holder carriage with respect to the supra-proximal drill guide holder carriage. The supra-proximal drill guide holder carriage is further adapted to translate the first and second supra-proximal drill guide holders parallel to the central axis of the intramedullary medical device and registered to a third supra-proximal position located proximally with respect to the proximal anchor element.

In another aspect, the disclosure describes an installation assembly for installing an intramedullary medical device into a patient including, in one embodiment, a proximal drill guide holder registered to a proximal anchor element of an intramedullary medical device, a distal drill guide holder registered to a distal anchor element of the intramedullary medical device, and a distal anchor element lock attached to the distal drill guide holder and adapted to connect with the distal anchor element. The installation assembly further includes a first compression assembly connecting the distal drill guide holder and the proximal drill guide holder and adapted to translate distally both the distal drill guide holder and the distal anchor element lock with respect to the proximal drill guide holder. The installation assembly further includes a supra-proximal drill guide holder registered to a supra-proximal position located proximally relative to the proximal anchor element, and a second compression assembly connecting the supra-proximal drill guide holder and the proximal drill guide holder and adapted to translate the proximal drill guide holder proximally with respect to the supra-proximal anchor drill guide holder.

In another aspect, the disclosure describes an embodiment of a planar telescoping intramedullary medical device installation assembly, including an intramedullary medical device interface adapted to hold an intramedullary medical device having a central axis within the intramedullary medical device installation assembly. The planar telescoping intramedullary medical device installation assembly further includes a first telescoping assembly with a first distal drill guide holder, a first proximal drill guide holder, and a first supra-proximal drill guide holder each of which is adapted to hold a drill guide in a drill plane that includes the central axis, and a second telescoping assembly with a second distal drill guide holder, a second proximal drill guide holder, and a second supra-proximal drill guide holder each of which is adapted to hold a drill guide in the drill plane. The planar telescoping intramedullary medical device installation assembly further includes a distal drill guide holder carriage adapted to hold the first distal drill guide holder to the second distal drill guide holder in the drill plane and in a distal registered position relative to a distal anchor element of an intramedullary medical device. The planar telescoping intramedullary medical device installation assembly further includes a proximal drill guide holder carriage adapted to hold the first proximal drill guide holder to the second proximal drill guide holder in the drill plane and in a registered position relative to a proximal anchor element of the intramedullary medical device. The planar telescoping intramedullary medical device installation assembly further includes a supra-proximal drill guide holder carriage adapted to hold the first supra-proximal drill guide holder to the second supra-proximal drill guide holder in the drill plane and in a registered position relative to a proximal anchor element of the intramedullary medical device. The first distal drill guide holder and the second distal drill guide holder share a distal axis that is perpendicular to the central axis. The first proximal drill guide holder and the second proximal drill guide holder share a proximal axis that is perpendicular to the central axis. The first supra-proximal drill guide holder and the second supra-proximal drill guide holder share a supra-proximal axis that is perpendicular to the central axis.

A BRIEF DESCRIPTION OF THE DRAWINGS

FIG. 6 is an exploded perspective view of one embodiment of a stop wheel for limiting proximal travel of a slideable interface lock.

DETAILED DESCRIPTION

The following description of various embodiments is merely exemplary in nature and is in no way intended to limit the disclosure. While various embodiments have been described for purposes of this specification, various changes and modifications may be made which will readily suggest themselves to those skilled in the art, and which are encompassed in the disclosure.

Unless otherwise indicated, all numbers expressing quantities, measurements (e.g., strains, stresses), properties, and so forth used in the specification and claims are exemplary and are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the claims are approximations, the numerical values set forth in the specific examples are reported as precisely as possible. Any numerical value, however, will inherently contain certain errors necessarily resulting from the standard deviation found in its testing measurements.

As used herein, the terms "proximal," "distal," "medial," and "lateral" relate to standard anatomical reference directions.

Figure 1:
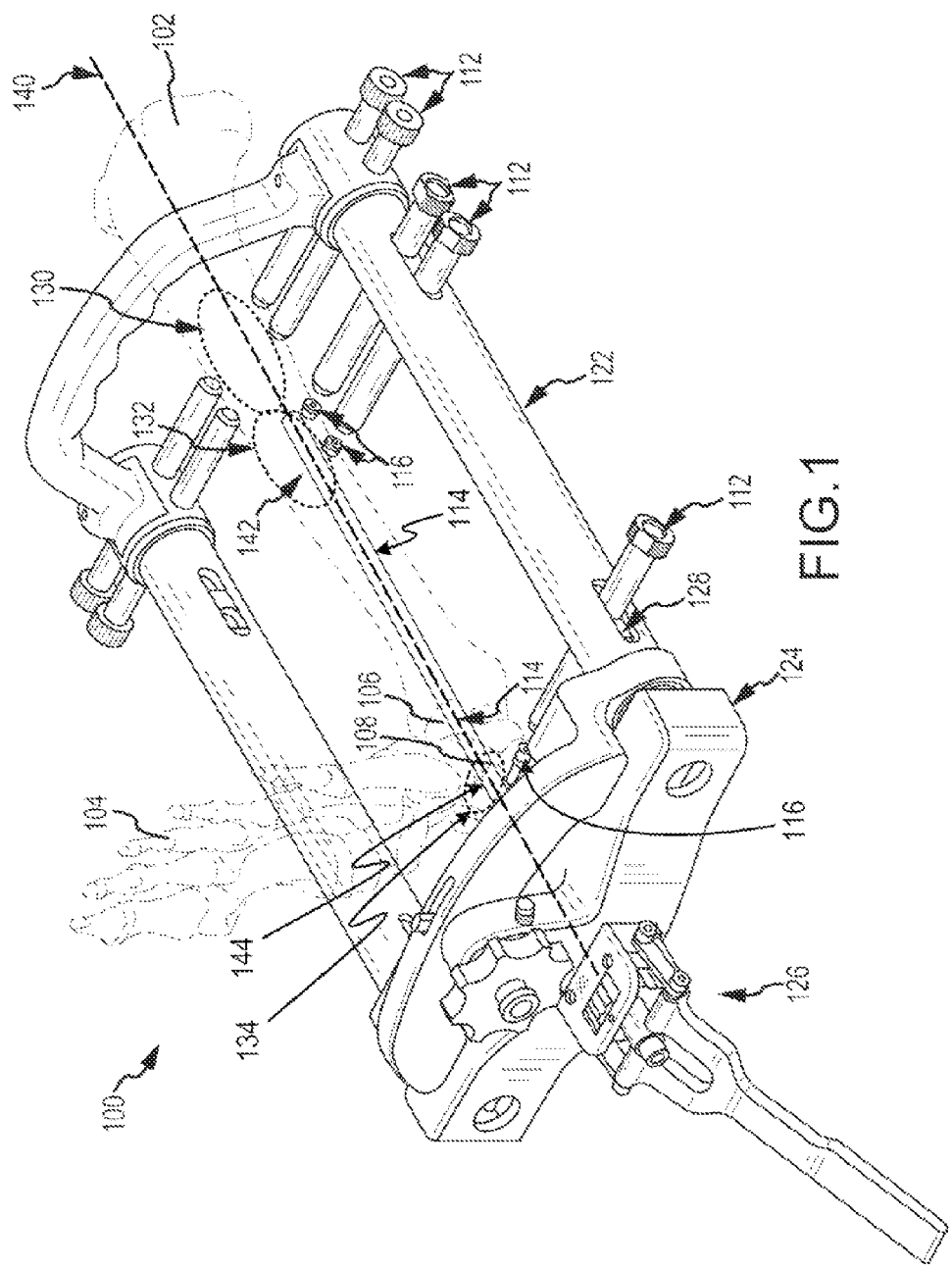
FIG. 1 is a perspective view of an intramedullary medical device installation assembly according to the present disclosure adapted for installing an exemplary intramedullary medical device within a patient's tibia, talus, and calcaneus to aid in an exemplary TTC procedure.

FIG. 1 is a perspective view of an intramedullary medical device installation assembly 100 according to the present disclosure adapted for installing an exemplary intramedullary medical device 114 (shown in broken lines) within a patient's tibia 102, talus 106, and calcaneus 108 to aid in an exemplary tibio-talo-calcaneal ankle fusion procedure. The intramedullary medical device 114 is attached to the patient's bones 102, 106, 108 using bone anchors 116 at various points as will be described further herein. The patient's foot bones 104 are shown generally to orient the reader to the correct placement of the intramedullary medical device 114 in this exemplary procedure.

A TTC procedure is a procedure utilized to permit the bones in the ankle of a patient to fuse over time. In an exemplary TTC procedure, the tibia 102, talus 106, and calcaneus 108 are held against each other and boney in-growth between the bones is facilitated. The boney in-growth is facilitated through an intramedullary medical device 114. An intramedullary medical device 114 is positioned inside a bore created in a patient's tibia 102 (e.g., within the medullary canal of the tibia 102, roughly along the long axis 140 of the tibia 102) and anchored proximally via a bone anchor 116 such as a bone screw. The procedure may create substantially parallel (e.g., coaxial) bores in the patient's talus 106 and calcaneus 108, allowing the intramedullary medical device to pass through the two bones on the way to the proximal anchor site 132 in the patient's tibia 102. Additional bone anchors 116 (e.g., bone screws) may be placed in the patients calcaneus 108, thereby allowing the intramedullary device to hold the patient's tibia 102, talus 106, and calcaneus 108 under compression while the bones fuse over time. As described further herein, bone anchor(s) 116 may be placed in the patient's tibia 102 before or after a bone anchor(s) 116 is placed in the patient's calcaneus 108.

Boney in-growth is achieved over time in a TTC procedure and the process of boney in-growth may result in the interfaces between bones compressing (e.g., as old bone compacts/resorbs, as new bone is formed) thereby resulting in a shortening of the distance between bone anchors. The compressing of bone interfaces and/or shortening of distance between bone anchors may result in a loss of the compressive stress (e.g., "compression") between bones provided by the intramedullary medical device 114. A loss of compression between the bones may result in an unsuccessful or prolonged fusion time for the bones and should otherwise be avoided. The intramedullary medical device 114 described herein limits the loss of compressive stress across bone interfaces due to a shortening of distance between bone anchors and thereby provides improved opportunities for bone fusion while boney in-growth occurs.

Intramedullary medical devices may be used in applications other than TTC procedures. For example, bones in the hand or foot may be fused using an intramedullary medical device and installation assembly, as described herein, but which has been sized and/or shaped appropriately for the smaller bones. Other bones which form joints may also be fused through suitable sizing and shaping of an intramedullary medical device and installation assembly as described herein. As another example, vertebrae in the spine may be fused.

Fractured bones may be held or set using an intramedullary medical device and installation assembly, as described herein. For example, a fracture in a long bone (e.g., tibia, femur, humerus, ulna) may be held or set using an intramedullary medical device. Fractures in other bones may also be held or set. An intramedullary medical device that is used to hold or set a bone fracture may be sized and/or shaped based on the size and/or shape of the fractured bone and/or intramedullary installation procedure and assembly used for the fractured bone. Different processes of bone growth may be facilitated through different levels of stress applied to the bones and/or fractured portions of bone. For example, bone fractures may be fused through the use compressive stresses that are different from the stresses used for fusing bones in a joint.

In one embodiment, bone anchors 116 are placed in a medial-lateral direction in the patient's tibia and calcaneus. Bone anchors 116 may be placed in an anterior-posterior direction, or on an angle to a medial-lateral direction and/or anterior-posterior direction. The illustration herein of bone anchors 116 placed in a medial-lateral direction is not meant to limit the disclosure or any claim to a particular placement direction of bone anchors 116.

In an exemplary TTC procedure, the proximal anchor element 142 of the intramedullary medical device 114 is anchored to the proximal site 132 (shown with dashed lines) in the patient's tibia 102 and a distal anchor element 144 of the intramedullary medical device 114 is fixed to the distal site 134 (shown with dashed lines) after the proximal anchor element 142 has been fixed to the patient's tibia 102. As another example, the distal anchor element 144 is fixed to the distal anchor site 134 before the proximal anchor element 142 has been fixed to proximal site 132 of the patient's tibia. A contracting element, also described herein as a "compression element," inasmuch as it applies compression between bones, connects the proximal anchor element 142 and the distal anchor element 144 and holds the bones under compression while the boney in-growth and fusion process occurs.

The term "fixed," as used herein with relation to an element of an intramedullary medical device 114 being fixed to a bone, refers to the attachment of the element of the intramedullary medical device 114 being substantially attached to the bone through the use of a bone anchor 116 or other means.

In one embodiment, strain may be induced into a compression element through stretching the compression element before both the distal anchor element 144 and the proximal anchor element 142 are fixed to the patient's bone(s). In an exemplary TTC procedure, the recovery of the strain in the compression element may occur while boney in-growth occurs between the patient's tibia 102, talus 106, and calcaneus 108. The compression element provides compression between the tibia 102, talus 106, and calcaneus 108 while the boney in-growth occurs, despite a decrease in distance between the proximal anchor site 132 and distal anchor site 134. The compression that is maintained between the tibia 102, talus 106, and calcaneus 108 increases the chances of a successful fusion between the bones.

As used herein, the term "strain" (when used without a qualifier) is used to refer to engineering strain, or the local axial distortion of a material divided by the length of that material along the axis of distortion. Strains as referred to herein are therefore dimensionless. The term "absolute strain" is used herein to refer to distortion expressed in units of length.

In the intramedullary medical device installation assembly 100, drill guides 112 help position and guide a drill, and facilitate placement of bone anchors 116 in the bones of the patient. Additional radiographic or other imaging techniques may be used for positioning bones and/or elements of the installation assembly 100 throughout the surgical process. To facilitate imaging procedures, any portion of the intramedullary medical device installation assembly 100 may be made from radio-transparent materials, such as carbon fiber or polymer resin, as appropriate.

In one embodiment, the intramedullary medical device installation assembly 100 includes four substructures including a supra-proximal structure 122, a proximal structure 124, a compression structure 126, and a distal structure 128. The supra-proximal structure 122 and the proximal structure 124 slideably interconnect with each other, as further described herein, and may provide compression across the ankle joint of a patient, including particularly the joints between the tibia 102 and the talus 106 and the calcaneus 108. This compression of the joint may be referred to herein as inter joint site reduction, surgery site reduction or simply joint reduction. In one embodiment, the proximal structure 124 and the distal structure 128 slideably interconnect through the compression structure 126 to allow a physician to compress a compression element of the intramedullary medical device 114, as described further herein.

A supra-proximal site 130 is shown (with dashed lines) on the patient's tibia 102. The supra-proximal site 130 may be accessed by drill guides 112 which are held by the supra-proximal structure 122. The supra-proximal structure 122 may be used to move the drill guides 112 along the long axis 140 of the intramedullary medical device and adjust the position of the supra-proximal site 130 relative to other structures such as the proximal structure 124 and the distal structure 128, particularly after the supra-proximal structure 122 has been fixed to the tibia 102. A proximal site 132 is shown on the patient's tibia 102 and is accessed by drill guides 112 held by the proximal structure 124. This proximal site 132 may be translated along the long axis 140 with respect to the supra-proximal site 130 and the distal site 134 by arranging, sliding, and applying forces between the supra-proximal structure 122, the proximal structure 124 and the distal structure 128. These relative movements will be described further herein.

The proximal site 132 is generally defined by the area on the patient's tibia 102 around the proximal anchor element 142 of the intramedullary medical device 114. The proximal site 132 is accessed by drill guides 112 held by the proximal structure 124 allowing a physician to access the patient's tibia 102 in the correct area to place bone anchors 116 fixing the proximal anchor element 142 to the patient's tibia. Therefore, as described further herein, the proximal structure 124 may hold drill guides 112 in a registered position with respect to the proximal anchor element 142 as each respectively travel along and parallel to the long axis 140.

The term "registered," as used herein, relates to a fixed relative positional relationship between elements, such as the registration marks and registration techniques used in semiconductor fabrication techniques to align one or mask(s) with a semiconductor wafer during processing.

A distal site 134 is shown on the patient's calcaneus 108. The distal site 134 is defined with respect to a distal anchor element 144 of the intramedullary medical device 114. The distal anchor element 144 may be fixed to the patient's calcaneus 108 at the distal site 134 through a bone anchor 116 placed through drill guide 112 that is held by the compression structure 126. The inner workings of the distal structure 128 as slideably connected with the proximal structure 124 and in the embodiment shown partially disposed inside the proximal structure 124 will be described further herein. The drill guide 112 held by the distal structure 128 is held in a registered position along the long axis 140 with respect to the distal anchor element 144 such that the drill 112 will allow a physician to access the distal element 144 as the distal anchor element 144 moves along the long axis 140, also as further described herein.

Reference to terms such as proximal, distal and compression to describe the supra-proximal structure 122, the proximal structure 124, the compression structure 126, and the distal structure 128 are meant only to illustrate the embodiments described herein and are not meant to limit the scope of the overall description. As one example, other embodiments may be possible where the functions of the supra-proximal structure 122 are performed by a structure located distally with respect to other structures of an intramedullary medical device installation assembly. As another example, a structure performing the same functions as the proximal structure 124 may, in other embodiments, be located more proximally than other structures of the intramedullary medical device installation assembly.

Figure 2:
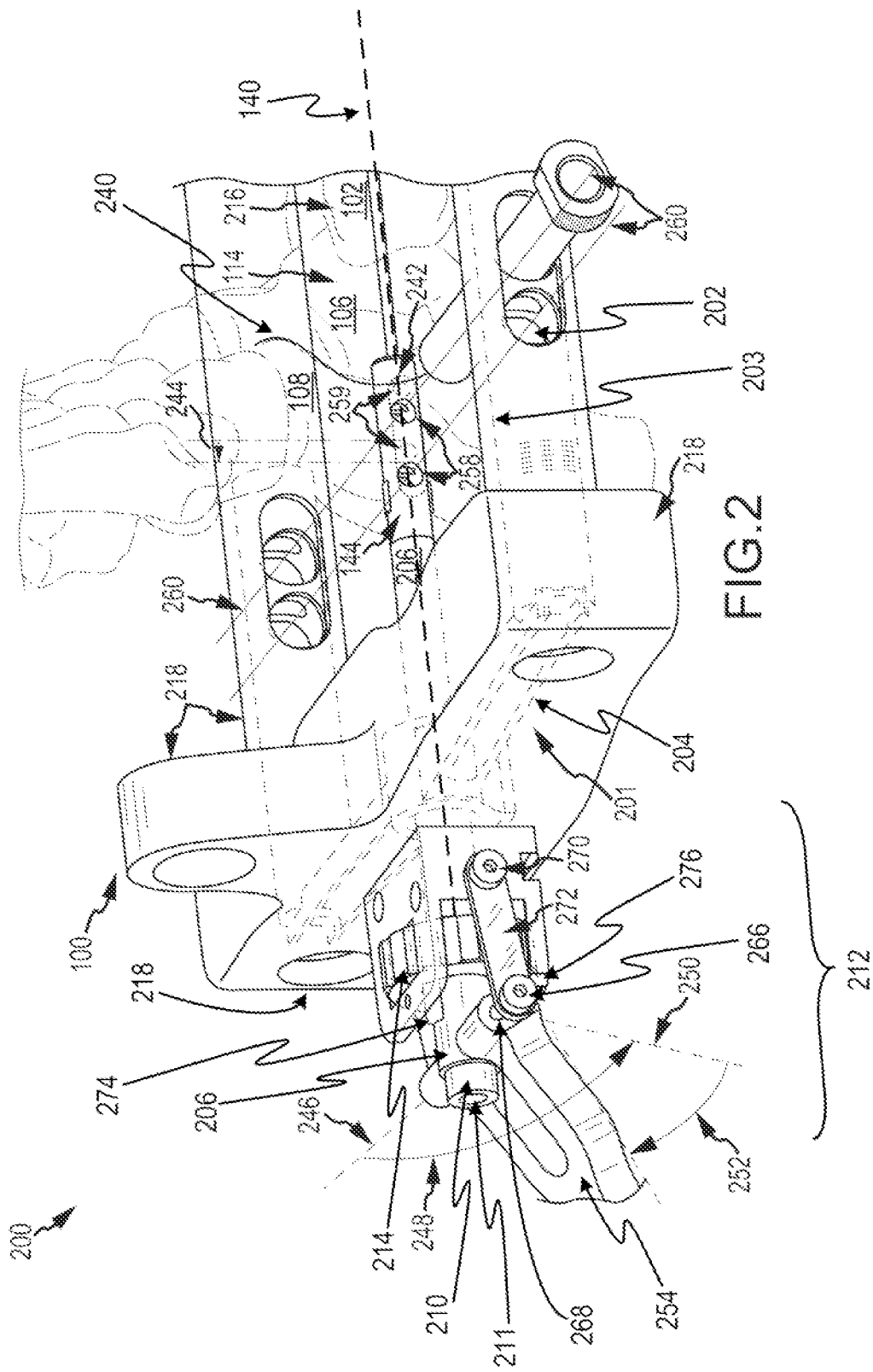
FIG. 2 is an enlarged perspective view of the a compression structure and a portion of a distal structure (shown in phantom) of an intramedullary medical device installation assembly shown in FIG. 1.

FIG. 2 is an enlarged perspective view of the a compression structure 200 and a portion of a distal structure 201 (shown in phantom) of the intramedullary medical device installation assembly 100 shown in FIG. 1. The distal structure 201 includes a drill guide support 203 and a drill guide holder 202 that are registered to a distal site 134 along a long access 140 of an intramedullary medical device 114. In one embodiment, the compression structure 200 includes lever assembly 212 for providing and controlling forces between the distal structure 201 and proximal structure components 218.

In one embodiment of the distal structure 201, the centers of the drill guide holders 202 are aligned with distal anchor element anchoring positions 260 which are further aligned with bone anchor interfaces 258 of the distal anchor element 208. The drill guide holders 202 are held in a registered position with respect to the bone anchor interfaces 258 as they are moved the long access 140. A distal structure sliding interface 206 is slideably interconnected with the proximal structure components 218. In one embodiment, the drill guide holder carriage 204 is slideably interconnected with the proximal structure components 218 through being attached to the distal structure sliding interface 206. The distal structure sliding interface 206 is attached to the distal anchor element 208 through a distal anchor element lock 210. In one embodiment, the distal anchor element lock 210 travels inside the proximal structure components 218.

The drill guide holder carriages described herein may take many forms, in different embodiments. For example, a drill guide holder carriage may be a brace member, a cross beam support, and/or a linkage. Further, a drill guide holder carriage may be formed with a drill guide support and/or a drill guide holder, as a single element or may formed as multiple connected separate elements.

In an exemplary installation procedure, a physician inserts the intramedullary medical device 114 into the ankle of the patient (including the calcaneus 108, the talus 106 and the tibia 102) while it is connected and attached to proximal structure components 218 and locked to the distal anchor element lock 210. The physician will align a proximal surface of the distal anchor element access port 242 with a proximal surface of the calcaneus 240. Particularly, in one embodiment, the physician may align the distal anchor element access port 242 with the subchondral bone of the posterior facet of the calcaneus 108. With the bone anchor interfaces 258 in their original positions 259, the most proximal bone anchor interface 258 will therefore be placed within the patient's calcaneus 108. Furthermore, using this technique, the compression distance 244 traveled by the bone anchor interfaces 258 during the process of setting compression in intramedullary medical device 114 will not move the bone anchor interfaces 258 outside of the patient's calcaneus 108. Indeed, a physician may guide the bone anchor interfaces 258 along the long axis 140 as far as the compression distance 244 to place the bone anchor interfaces 258 within a central portion of the patient's calcaneus 108.

After the compression has been set in intramedullary device 114 the bone anchor interfaces 258 have translated distally the compression distance 244 from their original positions 259. Furthermore, as described further herein, drill guide holders 202 have translated a commensurate distance parallel to the long axis 140 to the compression distance 244 travelled by the bone anchor interfaces 258, thereby maintaining a registered position with the bone anchor interfaces 258. As described further herein, the drill guide holder carriage 204 allows movement of the distal structure sliding interface 206 and the distal anchor element lock 210 to move both the drill guide holder carriage 204 and the drill guide holders 202 in a registered position with respect to the long axis 140. Therefore, after the bone anchor interfaces 258 have moved a compression distance 244, the drill guide holders 202 remain aligned with the distal anchor element anchoring positions 260.

A physician may use drill guide holders 202 to install bone anchors in the bone anchor interfaces 258. For example, the physician may use the drill guide holders 202 to position drill guides in order to drill holes in the calcaneus 108 and later to set bone anchors in the bone anchor interfaces 258. In one embodiment, there are two drill guide holders 202 on either side of the patient's ankle. This embodiment allows a physician to access a patient's ankle and particularly the patient's calcaneus 108 from either side depending on aspects of the particular surgery and/or the physician's preference.

The intramedullary medical device 114 allows two bone anchors to fix the distal anchor element 208 to the patient's calcaneus 108. In other embodiments, the distal anchor element 208 may have more bone anchor interfaces 258 or fewer. Additionally, in other embodiments, the number of drill guide holders 202 provided at similar positions along the long axis 140 may be adjusted. For example, drill guide holders 202 may be provided on only one side of the intramedullary medical device installation assembly. In other embodiments, the number of drill guide holders 202 on any side of the intramedullary medical device installation assembly may be modified to correspond to a different number of bone anchor interfaces 258 in the distal anchor element 208.

The lever assembly 212 allows a physician to provide forces against the distal structure sliding interface 206 that cause both the distal anchor element 208 and the drill guide holder carriage 204 to move along the long access 140 relatively to the proximal structure components. During this movement caused by the lever assembly 212, the drill guide holder carriage 204 moves along the long access 140 with an equal distance of translation to the distal structure sliding interface 206. The drill guide holders 202 move with the drill guide holder carriage 204 the same distance parallel to the long access 140. Therefore, the drill guide holders 202 maintain a registered position with respect to the bone anchor interfaces 258 of the distal anchor element 208 with respect to the long access.

The intramedullary medical device installation assembly described herein allows a physician to provide varying degrees of compression (e.g., varying forces and/or distances of compression) along a patient's joint through the bone fusion process. One embodiment of the compression structure 200 is described herein that includes a lever assembly 212 to configure the intramedullary medical device 114 to provide compressive forces to aid the bone fusion process. The term "compression" should be understood from the perspective of the intramedullary medical device 114 providing compression to a patient's bones. It should be not be construed to limit elements of either the intramedullary medical device 114 or the intramedullary medical device installation assembly to particular directions or forces within the intramedullary medical device or the intramedullary device or the intramedullary medical device installation assembly. For example, the intramedullary device 114 may include elements that are stretched or compressed in order to provide compression to the bones of a patient.

The total movement of the bone anchor interfaces 258 from their original positions 259 corresponds to this compression distance 244. As described further herein, the compression distance 244 may be set through multiple movements, including straining and releasing strain from portion(s) of the intramedullary medical device 114. The distal anchor element anchoring positions 260 have moved with these bone interfaces 258 and the drill guide holders 202 have moved commensurately through the same compression distance 244 parallel to the long access 140.

The intramedullary medical device 114 may be configured to provide compression to a patient's bone through the compression structure 200 utilizing a lever assembly 212. In one embodiment, the lever assembly 212 is connected to the proximal structure components 218 through a proximal structure interface 270 connected to a pivot arm 272 of the lever assembly 212. The pivot arm 272 attaches to a lever arm 254 at a pivot screw 266 of the lever assembly 212. The lever arm 254 includes a distal structure interface 268 that is offset from the pivot screw 266 thereby creating a load arm of the lever assembly 212. The lever arm 254 acts as the effort arm of the lever assembly 212 thereby providing substantial leverage on the distal structure sliding interface 206. In one embodiment the pivot screw 266, the pivot arm 272 and the proximal structure interface 270 are adapted to allow the lever assembly 212 to translate the distal structure interface 268 along the long axis 140 while the lever arm 254 is actuated by a physician.

Upon actuation of the lever assembly 212 by a physician, the distal structure sliding interface 206 is moved proximally or distally along the long axis 140. This distal structure sliding interface 206 is connected to the distal anchor element lock 210 (e.g., through friction, through screw threads, through normal forces on opposing flat surfaces) such that the distal anchor element lock 210 moves with the distal structure sliding interface both proximally and distally.

In one embodiment, the distal anchor element lock 210 may be connected with the distal structure sliding interface 206 solely through forces provided by and against elements of the intramedullary medical device 114. For example, the distal anchor element 208 may apply forces in a proximal direction and may thereby pull the distal anchor element lock 210 against a surface of the distal structure sliding interface 206, thereby holding those two elements together. In another embodiment, the distal anchor element lock 210 may have a threaded interface with the distal sliding interface 206, thereby allowing the two elements to be locked regardless of any forces exerted either proximally or distally by the distal anchor element 208.

The distal anchor element lock 210 is connected to the distal anchor element 208 and disposed within the distal structure sliding interface 206 and proximal structure components 218. The distal anchor element lock 210 may connect with the distal anchor element 208 through a number of connection structures and means, including, for example, screw threads and/or latches.

In one embodiment, the distal anchor element lock 210 includes a hex wrench interface 211 and the distal anchor element lock 210 connects with the distal anchor element 208 through a system of screw threads. The distal anchor element 210 may thereby be selectively connected by a physician to the distal anchor element 208 and may form a portion of the connection between the intramedullary medical device 114 and the intramedullary medical device installation assembly. Other elements and aspects of interfaces between the installation assembly and intramedullary medical device 114 are described further herein.

The lever assembly 212 acts to move the distal structure sliding interface 206 and the distal anchor element lock 210 proximally and distally. Through the distal anchor element lock's connection with the distal anchor element 208, the lever assembly 212 also moves the distal anchor element 208 proximally and distally. For example, the lever arm 254 may start at a first lever arm position 246 that corresponds to the distal structure sliding interface 206 and the distal anchor element lock 210 being in a position along the long access 140 whereby no compression is set in the intramedullary medical device 114. The distal anchor element 208 is shown with original positions 259 indicating a more proximal position of the bone anchor interfaces 258 when the intramedullary medical device 114 does not have any compression set within it. When the lever arm 254 is moved through a strain setting movement 248, the distal structure sliding interface 206 is moved distally along the long access 140 thereby moving the distal anchor element lock 210 and the distal anchor element 208 distally along the long access 140.

As part of the proximal structure components 218, a compression limit 276 is disposed in one embodiment such that the lever arm 254 will contact the compression limit 276 after a threshold amount of distal travel of the distal structure sliding interface 206 has been achieved. This threshold amount of distal travel may be enforced by the compression limit 276 in order to limit the amount of distal travel of the distal anchor element 208 to an acceptable or appropriate amount for the intramedullary medical device 114. For example, intramedullary medical device 114 may configured such that only a limited amount of distal travel of the distal anchor element 208 may be necessary or beneficial in the process of activating compression within the intramedullary medical device 114. Therefore, in one embodiment, the compression limit 276 may be set to limit travel of the lever arm 254 and commensurate distal travel of the distal structure sliding interface 206 to an amount of distal travel that will not damage and/or hinder the functioning of the intramedullary medical device 114.

In another embodiment, the compression limit may set a limit of distal travel to an amount necessary for achieving a proper activation of the compressive functions of the intramedullary medical device 114. For example, during a strain setting movement 248, distal movement of the distal anchor element 208 may cause strain in a shape memory alloy element of the intramedullary medical device 114 causing the shape memory alloy element to exhibit "pseudo-elastic" properties (also termed "super-elastic" properties) of the shape memory alloy. These pseudo-elastic properties may arise from transitions made between crystalline phases of the shape memory alloy (e.g., martensite to austenite, martensite to rhombohedral) without temperature restrictions (e.g., freezing of a crystalline phase) on the transitions.

In one embodiment, the strain setting movement 248 may be followed by a strain reducing movement 252. Release of the strain or "strain reducing" may be performed in order to select a desired amount of strain to be applied to the compressive element before the compressive load (or "stress") is applied to the bones of the patient. Adjustment of the strain may be performed in order cause a compressive element of the intramedullary medical device 114 to exhibit an unloading stress in an embodiment where the compressive element that exhibits hysteresis. In such an embodiment, it may be desired to have the compressive element begin exhibiting an unloading stress before the compressive load is transferred to the bones of the patient.

The strain reducing movement 252 may cause the shape memory alloy element of the intramedullary medical device 114 to move from a "loading stress" to an "unloading stress," embodied in the hysteresis of the shape memory alloy's pseudo-elastic properties. For example, after an initial strain is imparted through the strain setting movement 248, part of the strain may be released (e.g., through the strain reducing movement 252) in order to cause the compressive element to exhibit the unloading stress that will be placed across the joint construct after the intramedullary medical device 114 has been released from the intramedullary installation assembly 100.

In another embodiment, after the strain setting movement 248, the lever arm is in a second lever arm position 250, and there is no following strain reducing movement 252. In this embodiment, the bone anchor interfaces 258 may be accessed, and bone anchors may be attached in this position without the strain reducing movement 252.

In some embodiments, a compression element including shape memory alloy may be designed and/or adapted to be in the pseudo-elastic region for strains that are utilized in the fusing of bones. A TTC procedure allows bones to fuse over time, and there may be an expected amount of travel between the bone anchors due to the bone fusion process. A compression element including shape memory alloy may be designed such that the expected amount of travel may be smaller than the pseudo-elastic region, in terms of absolute strain of the contracting element. For example, a contracting element may exhibit pseudo-elastic behavior throughout a bone fusion process if the contracting element's pseudo-elastic region is exhibited over a larger absolute strain than the expected amount of travel of the bone anchors of the intramedullary medical device 114 during the bone fusing process. Some examples of absolute strain ranges corresponding to pseudo-elastic regions of compression elements may include 0 to 15 millimeters, 0 to 10 millimeters, 0 to 8 millimeters, 0 to 6 millimeters, 0 to 5 millimeters, 1 to 15 millimeters, 1 to 10 millimeters, 1 to 8 millimeters, 1 to 6 millimeters, and 1 to 5 millimeters. Any of these compressions may be applied by installation assemblies described herein for use with intramedullary medical devices adapted to apply these compressions during a TTC bone fusion process.

The strain-setting process 248 and strain-reducing processes 252 that are described further herein may place an absolute strain (e.g., the compression distance 244) on the compression element in order to configure the compression element to exhibit the pseudo-elastic properties. For example, an absolute strain of 10 millimeters may be imparted to the contracting element and then the absolute strain may be released to 7 millimeters. The absolute strain may then be released to 5 millimeters. In one embodiment, an absolute strain of 8 millimeters may be imparted before releasing the absolute strain to 5 millimeters. In other embodiments, an absolute strain of about 6 to about 20 millimeters may be imparted before releasing to a selectable absolute strain of between 8 millimeters and less than 1 millimeter, as selected using a selectable strain release stop, as described further herein.

Pseudo-elastic stress-strain curves may also be developed for compressive strains on a shape memory alloy. For any given shape memory alloy, the magnitudes of the compressive stresses and compressive strains may differ from the tension stresses and tension strains. As described further herein, configurations of the proximal and distal anchor elements 208 of the intramedullary medical device 114 may provide compression between those elements through the stored compressive strain in an element that provides compression to bones in a TTC bone fusion process through expanding (e.g., an expansive element). In other words, in such an expansive element, recovery of the compressive strain through expansion may be configured to provide compressive forces between the proximal anchor element and the distal anchor element 208 of an intramedullary medical device 114. As further described herein, the sustained compressive forces between the proximal anchor element and the distal anchor element provide medical advantages when used with patients (e.g., in a bone fusion application).

In one embodiment, the strain reducing movement 252 may be selectively limited by a physician, thereby allowing the physician control to the compression distance 244. For example, the physician may be able to control the proximal movement of the distal structure sliding interface 206 due to the strain reducing movement 252 through a system for selecting a limited amount of allowable proximal movement of the distal structure sliding interface 206.

In one embodiment, a system for limiting proximal movement of the distal structure sliding interface 206 includes a stop wheel 214 disposed around the distal structure sliding interface 206 and interfacing with (e.g., being held by) proximal structure components 218. The stop wheel 214 may be rotated by a physician after the distal structure sliding interface 206 is distally translated past a distal threshold, thereby allowing a sliding interface lock 274 to pass interior features of the stop wheel 214 that are described further herein. After the physician has rotated the stop wheel 214, and thereby selected an amount of proximal travel of the distal structure sliding interface 206 to be allowed during the strain reducing movement 252, the stop wheel 214 serves to block proximal translation of the sliding interface lock 274 past the selected amount. After the sliding interface lock 274 reaches the selected amount of proximal travel indicated by the position of the stop wheel 214, any further strain reducing movement 252 will be inhibited and the distal anchor element 208 will have the physician selected amount of absolute compressive strain (e.g., compression distance 244).

FIG. 6 is an exploded perspective view of one embodiment of a stop wheel 214 for limiting proximal travel of a slideable interface lock 274. The stop wheel 214 has a central barrel bore 278 adapted to fit the main shaft of the distal structure sliding interface 206. An axial offset within the bore 278 forms a lock slide channel 280 on the interior of the stop wheel 214 to allow a sliding interface lock 274 to pass through the stop wheel 214 when the stop wheel is positioned in certain rotational positions. For example, the stop wheel 214 may allow the slideable interface lock 274 to travel both proximally and distally past a stop wheel 214 when the physician has rotated the stop wheel 214 in order to allow the slideable interface lock 274 to travel proximally and distally without restriction. As one example, during a strain setting movement, described further herein, the physician may move the slideable interface lock 274 proximally through the stop wheel 214 through the lock slide channel 280 and past one or more of the lock stop points 282.

Subsequently, the physician may rotate the stop wheel 214 to a position indicated by distance indicators 284 on the outside of the stop wheel 214. After the stop wheel 214 is rotated, a sliding interface lock 274 will be positioned to abut one of the lock stop points 282 if the physician has selected a minimum compression distance that is greater than zero using the stop wheel 214. In this instance, a physician would be limited in moving the lever assembly 212 through a strain reducing movement that would move the sliding interface lock past the selected lock stop point 282. If, however, the physician selected a zero minimum compression distance, the slideable lock interface would again be oriented with the lock slide channel 280 and proximal travel of the sliding interface lock would not be inhibited by the stop wheel 214 in that position.

Figure 3:
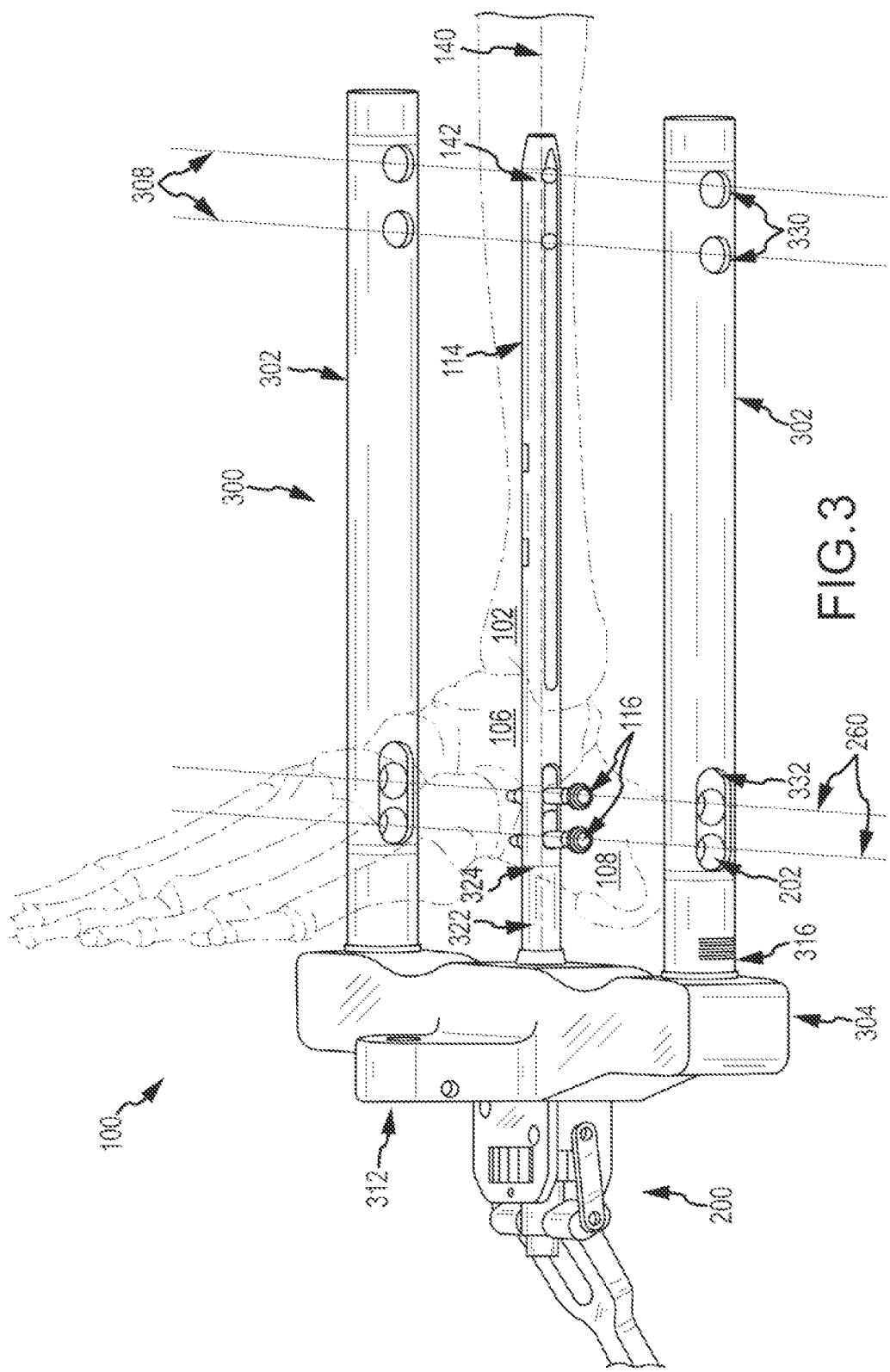
FIG. 3 is a separate perspective view of one embodiment of a proximal structure of an intramedullary medical device installation assembly shown in FIG. 1.

FIG. 3 is a separate perspective view of one embodiment of a proximal structure 300 of an intramedullary medical device installation assembly 100 shown in FIG. 1. The proximal structure 300 includes proximal structure drill guide holders 330 and proximal structure drill guide supports 302 connected by proximal drill guide holder carriage 304. The proximal structure 300 may maintain the drill guide holders 330 in registered positions with respect to the proximal anchor element 142, as described further herein. For example, the proximal drill guide holder carriage 304 is connected to the intramedullary medical device pedestal 322 that is adapted to connect to the proximal anchor element 142, for example through portions of the intramedullary medical device 114. Through connecting to the proximal anchor element 142, the proximal structure 300 may maintain registered positions of the proximal structure drill guide holders 330 with respect to the proximal anchor element 142, namely at proximal anchor element anchoring positions 308.

The proximal structure 300 is situated and disposed around portions of the compression structure 200 and distal structure 201. For example, distal structure drill guide holders 202 are shown within proximal structure drill guide supports 302. The distal structure drill holders 202 are accessible by a physician through the drill guide holder access ports 332. Other portions of the compression structure 200 and distal structure 201 are located distally to the proximal structure 300 and other elements of the compression structure 200 and distal structure 201 may be located within portions of the proximal structure 300, such as the distal drill guide holder carriage 204.

The drill guide access ports 332 are located in the proximal structure 300, and particularly within the proximal structure drill guide supports 302. In one embodiment, these drill guide access ports 332 may be adapted to limit the physician's ability to access the distal drill guide holders 202 when the distal anchor element 114 is not in a position that would indicate that the contracting element of the intramedullary medical device is not correctly set for compression. For example, the installation assembly 100 may allow the contracting element be strained (e.g., during a strain setting movement) to a particular strain (e.g., a maximum compression distance), as described further herein, that may be too large or otherwise beyond what is allowed or preferred for installing the intramedullary medical device (e.g., a maximum installed compression distance). As one example, the compression structure 200 may be adapted to allow straining of the contracting element to 10 millimeters, which may be beyond the allowable strain for installation of the intramedullary medical device. For example, the allowable strain for installation may be less than or equal to about 6 millimeters and the drill guide access ports 332 may only allow access to one or more of the drill guide holders when the range of allowable strains for installation is reached. Therefore, the installation assembly 100 and, in certain embodiments, particularly the proximal structure 300, may provide a range of allowable strains of the intramedullary medical device (e.g., within the contracting element) where one or more drill guide holder(s) are unavailable for placement of drill guides and/or drills, specifically, between a maximum compression distance and a maximum installed compression distance.

These disallowed strains for the intramedullary medical device by the installation assembly 100 (e.g., strains that are allowed to be imparted to the device, but not allowed to be installed) may range from less than 1 millimeter of disallowed strain up to about 20 millimeters of disallowed strain. For example, 2 millimeters of strain may be disallowed in the case where a contracting element in an intramedullary medical device 114 may be strained to about 8 millimeters and then the strain may need to be released to about 6 millimeters (or less) before installation may be allowed by the installation assembly 100. As described further herein, material processing considerations of the contracting element may dictate the minimum amount of released strain in the contracting element before installation of the device in order to achieve desirable pseudo-elastic stress-strain properties during the unloading curve of the contracting element. As other examples, less than 1 millimeter of released strain may be required and more than 4 millimeters of released strain (e.g., between 10 millimeters of applied strain and 6 millimeters of installed strain) may be required, depending on material processing of the contracting element. The disallowed range and allowed range of installation strains for the installation assembly 100 may be designed to achieve these stress-strain properties, to ensure the correct unloading stress is applied by the intramedullary medical device, and/or to allow physicians an appropriate level of discretion in the installation process, based on a patient's particular indications.

The proximal structure 300 may slideably interconnect with the distal structure 201 through the compression structure 200, as described further herein. Also as described further herein, the distal structure drill guide holders 202 may be used to position distal bone anchors 116 in the patient's calcaneus 108 at distal anchor element anchoring positions 260 along the long axis 140 of the intramedullary medical device 114.

In an exemplary embodiment of a surgical installation procedure for the intramedullary medical device 114, after the distal bone anchors 116 are set in a patient's calcaneus 344 and the distal anchor element anchoring positions 260 and the proximal anchor element anchoring positions 308 are maintained in a fixed relationship to each other relative to the long axis 140. A physician may fix the intramedullary medical device 114 to the patient's calcaneus 108 before compressing the patient's ankle joint construct by removing any distance between the patient's calcaneus 108, the patient's talus 106 and the patient's tibia 102. In this exemplary procedure, the compression of the patient's joint construct, described further herein, moves the patient's calcaneus 108 and the distal anchor element anchoring positions 260 proximally along the long axis 140. In addition, the intramedullary medical device 114 is moved proximally along the long axis 140 an equal distance. The proximal structure 300 may be used to move the intramedullary medical device 114 proximally along the long axis 140 while also moving the proximal anchor element anchoring positions 308 and the proximal structure drill guide holders 330 an equal distance along the long axis 140 to maintain a registered position between the proximal structure drill guide holders 330 and the proximal anchor element 142.

In an exemplary embodiment, the proximal structure 300 includes a proximal to supra-proximal structure slideable interface support 312. In one embodiment, the proximal to supra-proximal slideable interface support 312 is located on a distal portion of the proximal structure 300 and attaches to a distal portion of a supra-proximal structure of the intramedullary medical device installation assembly. For example, the proximal to supra-proximal structure slideable interface support 312 may be located below a patient's foot during a surgical procedure. In other embodiments, the proximal to supra-proximal structure slideable interface support 312 may be located at other positions of the proximal structure 300 and/or may be adapted to take different forms.

The proximal structure 300 is adapted to slideably interface with a supra-proximal structure of the intramedullary medical device installation assembly 100. For example, the proximal structure drill guide supports 302 are adapted to slideably interconnect with drill guide supports of a supra-proximal structure of the intramedullary medical device installation assembly, as described further herein. In one embodiment, distance markings 316 may be provided to show relative movement between the proximal structure 300 and a supra-proximal structure of the intramedullary medical device installation assembly. In one embodiment of a surgical technique for installing an intramedullary medical device 328, the movement shown by the distance markings 316 may be commensurate with a reduction of distances within a patient's joint construct as the intramedullary medical device 114 and the proximal structure 300 are moved together proximally along the long axis 140.

The proximal structure 300 includes an intramedullary medical device pedestal 322 that includes an intramedullary medical device interface 324. The intramedullary medical device interface is adapted to connect with an otherwise interface with a distal end of the intramedullary medical device 114. The intramedullary medical device interface 324 may include keyed or registration features which perform anti-rotation functions such that the intramedullary medical device 114 is rotationally registered with respect to the proximal structure 300. For example, the intramedullary medical device when attached to the intramedullary medical device interface 324 may be held in a particular rotational position around a long axis 140. The intramedullary medical device interface 324 may include keyed or registration features that align the long axis 140 with the center of the intramedullary medical device pedestal 322 and parallel to the proximal structure drill guide supports 302. As one example, the intramedullary medical device interface 324 may include features that mate with a distal surface of the intramedullary medical device 114, including, for example, ridges and channels, flat planes and/or angled surfaces such as saw tooth structures, anti-rotation or key features of the intramedullary medical device interface 324 may allow the intramedullary medical device 114 to fit only in one rotational configuration or may allow multiple distinct and predetermined rotational configurations. For example, the intramedullary medical device 114 shown in FIG. 3 may be adapted to connect with the intramedullary medical device interface 324 in either of two rotationally symmetric orientations with respect to the long axis 140 and offset by 180 degrees from each other. In an alternative embodiment, the intramedullary medical device interface 324 may be configured to connect with the intramedullary medical device 114 in only one rotational configuration without the ability to connect solidly with the intramedullary medical device 114 in any other rotational configuration with respect to the long axis 140.

Figure 4:
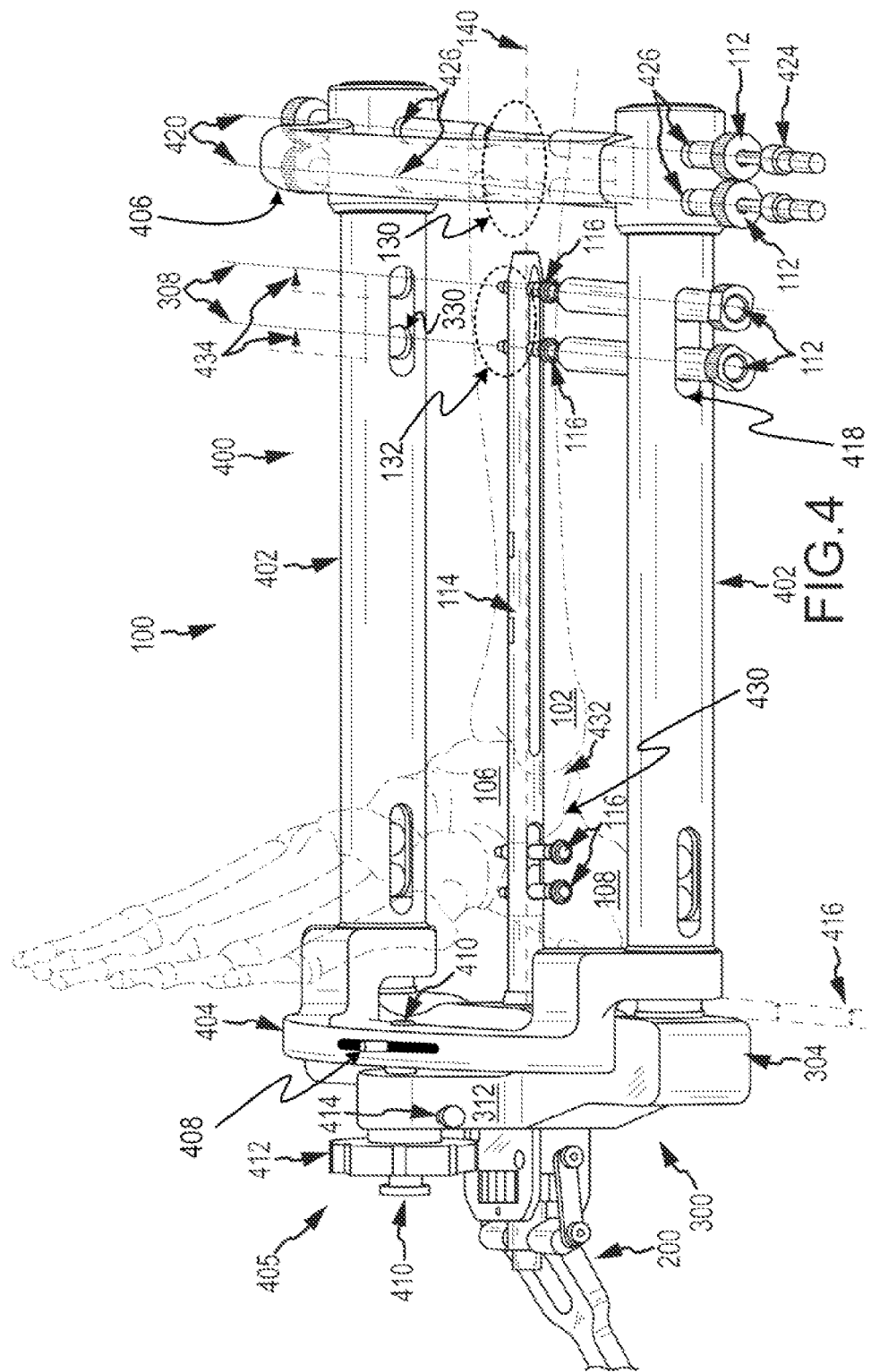
FIG. 4 shows an embodiment of a supra-proximal structure of an intramedullary medical device installation assembly, including a supra-proximal drill guide holder carriage and supra-proximal structure drill guide supports shown in FIG. 1.

FIG. 4 shows an embodiment of a supra-proximal structure 400 of an intramedullary medical device installation assembly 100, including a supra-proximal drill guide holder carriage 404 and supra-proximal structure drill guide supports 402 shown in FIG. 1. The supra-proximal structure 400 is slideably connected to the proximal structure 300 that is described further herein. The supra-proximal structure drill guide supports 402 carry supra-proximal drill guide holders 426 that are adapted to access a patient's tibia at a supra-proximal site 130 that is farther proximal along the patient's tibia than the proximal site 132 and the proximal anchor element anchoring positions 308, and therefore termed for the purpose of this description "supra-proximal."

The supra-proximal structure 400 includes supra-proximal structure drill guide holders 426 and supra-proximal structure drill guide supports 402 connected by supra-proximal drill guide holder carriage 404. The supra-proximal structure 400 may maintain the drill guide holders 426 in adjustable position along to the long axis 140 of the intramedullary medical device 114 and the proximal anchor element 142, as described further herein. For example, the supra-proximal structure 400 is slideably connected to the proximal structure 300, as described further herein.

The supra-proximal structure 400 optionally includes a cross-support 406 shown connecting the supra-proximal structure drill guide supports 402 at a proximal end of the installation assembly. The cross-support 406 may be adapted to be attached and detached from the supra-proximal structure drill guide supports 402 in order to allow the installation assembly and the intramedullary medical device 114 to be inserted inside the patient's body while allowing the patient's foot to clear the area that would otherwise be crossed by the cross-support 406.

The supra-proximal drill guide holders 426 are adapted to position and hold supra-proximal drill guides 422 that guide in place supra-proximal drills 424 into the patient's tibia at supra-proximal bone anchor positions 420. The supra-proximal drills 424 are positioned in the patient's tibia in order to hold the patient's tibia 102 with respect to the intramedullary medical device installation assembly 100 while the intramedullary medical device 114 is positioned within the patient's tibia 102. By leaving the supra-proximal drills 424 in the patient's tibia 102 (e.g., for a portion of the surgical procedure), the physician may manipulate the intramedullary medical device 114 with respect to the patient's tibia 102. For example, the intramedullary medical device 114 may be moved proximally through a patient's tibia 102 while inter joint site reduction 430 and 432 is performed within the patient's ankle joint.

During this process, as described further herein, the proximal structure drill guide holders 330 remain registered to the proximal anchor element 142 of the intramedullary medical device 114 with each maintaining the proximal anchor element anchoring positions 308 with respect to the long axis 140 of the intramedullary medical device 114. In order to move the intramedullary medical device proximally through the patient's tibia 102, the proximal structure 300 of the intramedullary medical device installation assembly is moved proximally with respect to the supra-proximal structure 400 thereby decreasing the proximal to supra-proximal structure distance 416. With the supra-proximal bone anchor positions 420 fixed against the patient's tibia 102 through supra-proximal drills 424, reducing the proximal to supra-proximal structure distance 416 moves the intramedullary medical device proximally through the patient's tibia. In one embodiment, this movement provides for inter-joint site reduction 430 and 432 because the patient's calcaneus 108 is fixed to the intramedullary medical device 114 with distal bone anchors 116, as described further herein. In an exemplary embodiment of a surgical method, the distal bone anchors 116 are fixed to a patient's calcaneus 108 before inter joint site reduction 430 and 432 is completed and also before the proximal anchor element 142 of the intramedullary medical device 114 is fixed to the patient's tibia through proximal bone anchors 116.

The proximal to supra-proximal structure distance 416 is reduced in one embodiment of the intramedullary medical device installation assembly through a slideable interface 405 between the proximal structure 300 and the supra-proximal structure 400. As described further herein, a slideable interface 405 between the proximal structure and the supra-proximal structure may allow for a physician to controllably reduce the proximal to supra-proximal structure distance 416 while observing and controlling the inter-joint site reduction 430 and 432 to radiographic or other imaging techniques. In one embodiment, the slideable interface 405 between the proximal structure 300 and the supra-proximal structure 400 includes a threaded interface between a rod 410 and a wheel 412 designed to be operated by hand by the physician. In one embodiment, the rod 410 may be moved proximally or distally through rotating the wheel 412 and thereby moving the supra-proximal structure 400 with respect to the proximal structure 300.

In one embodiment, the slideable interface 405 includes a lock pin 414 that allows the slideable interface 405 to be removed from the proximal structure 300. The slideable interface 405 may include a proximal to supra-proximal structure slideable interface lock 408 that allows the rod 410 to be connected or disconnected from the supra-proximal structure 400. Either or both of the locking pin 414 and the proximal to supra-proximal structure slideable interface lock 408 may be provided to give a physician flexibility in assembling or disassembling the intramedullary medical device installation assembly during a surgical procedure while decreasing the possibility of needing to remove the proximal structure 300 from the intramedullary medical device 114 or needing to remove the intramedullary medical device 114 from the patient's body.

In one embodiment, a physician may place proximal anchor element drill guides 112 inside the proximal structure drill guide holders 330 in order to prepare holes in the patient's tibia 102 for installing proximal bone anchors 116 that will fix the proximal anchor element of the intramedullary medical device 114 to the patient's tibia 102. A proximal anchor element is fixed through the proximal anchor element anchoring positions 308 after inter-joint site reduction 430 and 432 is performed through reducing the proximal to supra-proximal structure distance 416, as described further herein. Inter-joint site reduction 430 and 432 may result in proximal drill guide holders 330 translating proximally in registered position(s) to the proximal anchor element 142. The proximal drill guide holders 330 may be accessed through an access port 418 in the supra-proximal drill guide supports 402, and will travel a commensurate distance 434 within the access ports 418 to the inter-joint site reduction 430 and 432.

After the proximal bone anchors 116 fix the patient's tibia 102 to the proximal anchor element 142 of the intramedullary medical device 114, the installation assembly may transfer the compressive load of the compression element inside the intramedullary medical device 114 to the patient's bones 108, 106, and 102. As described further herein, the compression structure 200 of the installation assembly may hold the compressive load of the compression element of the intramedullary medical device 114 against other portions of the intramedullary medical device 114 while the installation process is performed. The compression structure 200 and the proximal structure may hold these compressive forces between them allowing the intramedullary medical device 114 to be positioned by the physician inside a patient's body without the compressive forces interfering with the positioning process.

Figure 5:
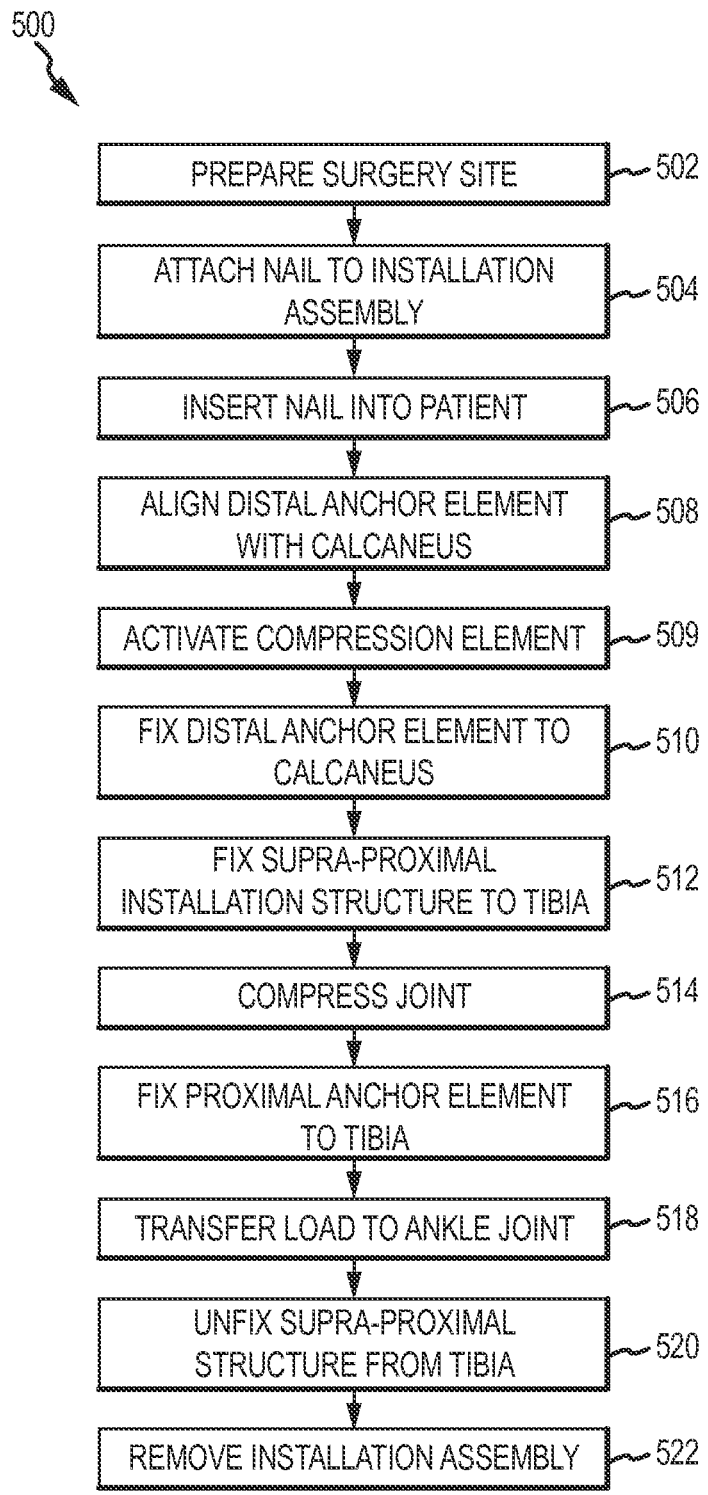
FIG. 5 shows a flow chart of an exemplary embodiment of a surgical method for installing an intramedullary medical device inside a patient.

FIG. 5 shows a flow chart of an exemplary embodiment of a surgical method 500 for installing an intramedullary medical device 114 inside a patient. The method 500 begins in position 502 wherein the surgery site is prepared 502. This preparation process 502 will be understood by those with skill in the art to include preparations of the ankle joint for fusion including alignment of the bones such as reaming of the medullary canal of the tibia 102, and debriding of the surfaces of the ankle joint. Next, in operation 504, the physician may attach the intramedullary medical device 114 to the installation assembly 100. In one embodiment, attachment 504 of the device 114 may be performed before the surgery is initiated. In another embodiment, attachment 504 of the device 114 may be performed after the surgical site is prepared in operation 502 and after the physician has made preliminary measurements about the length of the intramedullary medical device to be used in the procedure. With the intramedullary medical device 114 attached 504 to the installation assembly 100, the intramedullary medical device 114 may be inserted into the patient in operation 506. The connection of the intramedullary medical device 114 to the installation assembly 100 as described further herein may provide particular alignment features for the intramedullary medical device during its insertion 506 into the patient. For example, the connection between the installation assembly and the intramedullary medical device may require and/or create a particular rotational relationship and thereby provide the physician with control over the rotational positioning (e.g., around the long axis, perpendicular to the long axis) during the insertion in operation 506 into the patient.

After the intramedullary medical device is inserted in operation 506 into the patient, the physician may align, in operation 508, the distal anchor element access port relative to the patient's calcaneus, as described further herein. In this alignment operation 508 performed by the physician, he or she may use radiographic techniques or other appropriate means to view the intramedullary medical device 114 inside the patient relative to the patient's calcaneus 108.

In the next operation 508 of the surgical procedure, the distal anchor element access port may be aligned such that a proximal surface of the distal anchor element access port coincides with a proximal portion of the patient's calcaneus 108, such as the subchondral bone of the posterior facet of the calcaneus. In other embodiments, a physician may perform alternate alignments that are adapted to achieve consistent and effective fixations to the patient's calcaneus. For example, in embodiments with large compression distances, this alignment operation 508 may be made at a distance farther proximal than at a portion of the calcaneus 108.

After the distal anchor element access port is aligned in operation 508 with a patient's calcaneus, the compressive element of the intramedullary medical device 114 is activated in operation 509 through actions of the installation assembly described further herein. The activation operation 509 may include multiple processes or sub-steps and is described further herein. In one embodiment, the activation in operation 509 of the compression element is performed after the distal anchor element port is aligned in operation 508 with the patient's calcaneus 108.

In another embodiment, the compression element may be activated in operation 509 before the distal anchor element port is aligned in operation 508 with the patient's calcaneus 108. For example, after a compression element is activated in operation 509 within the intramedullary medical device, bone anchor interfaces of the distal anchor element may be aligned with a central portion of the patient's calcaneus as determined by the physician in order to ensure a consistent and acceptable fixation to the calcaneus. In alternative embodiments, the compression element of intramedullary medical device may be activated 509 before the intramedullary medical device is inserted 506 into the patient. Thus, the particular order of operations in method 500, including operation 506-509, may be varied depending on the physician's needs in a particular surgical procedure.

In one embodiment, after the compression element is activated in operation 509, the distal anchor element is fixed in operation 510 to the patient's calcaneus. The physician may choose to perform the fixing in operation 510 after the activation in order to establish the position of the distal anchor element 144 accurately within the calcaneus 108 before proceeding with the fixing in operation 510 of the intramedullary medical device 114 to the calcaneus. As described further herein, the distal anchor element 144 and/or related structures may be aligned with proximal portions of the calcaneus with the expectation that the activation operation 509 will move the distal anchor element distally into a more suitable fixation site (e.g., near the center) of the calcaneus.

In another embodiment, the distal anchor element is fixed in operation 510 before the compression element is activated in operation 509. In this alternative embodiment, the physician may choose to fix 510 the distal anchor element at a desired position on the calcaneus and then activate 509 the compression element. This subsequent activation operation 509 may translate the calcaneus distally and may require further inter-joint site reduction, as described further herein. However, the physician may choose this embodiment to achieve other goals.

Alternatively, after the compression element is activated in operation 509, the supra-proximal structure 400 of the intramedullary medical device installation assembly 100 is fixed in operation 512 to the tibia of the patient. As described further herein, the operation 512 of fixing the supra-proximal structure 400 may be performed through inserting bone drills 424 through drill guides 112 held by the supra-proximal structure of the intramedullary medical device installation assembly 100 and into supra-proximal sites 130 in the patient's tibia 102. Also as described further herein, the bone drills 424 may be used to hold the patient's tibia 102 while the intramedullary medical device 114 is moved proximally through the patient's tibia and the patient's ankle joint is compressed using the intramedullary medical device installation assembly 100. In other embodiments, fixing the supra-proximal structure 400 to the patient's tibia 102 in operation 512 through the use of supra-proximal bone drills may be performed before the compression element of the intramedullary medical device is activated in operation 509 and/or before the distal anchor element is aligned in operation 508 with the patient's calcaneus 108.

After the supra-proximal structure 400 is fixed in operation 512 to the patient's tibia, the physician may compress the ankle joint of the patient in operation 514 through inter-joint site reduction, as described further herein. In operation 514, compression of the joint of the patient may be performed using the intramedullary medical devise installation assembly 100 through moving the proximal structure 300 relative to the supra-proximal structure 400 through a slideable interface, as described further herein. A slideable interface may allow the physician to controllably compress the joint of the patient through moving the patient's calcaneus 108 proximally with respect to the patient's tibia, thereby compressing the patient's ankle joint along the long axis of the intramedullary medical device.

In one embodiment, with the ankle joint of the patient compressed through operation 514 to a sufficient degree as determined by the physician, the proximal anchor element 142 may be fixed in operation 516 to the patient's tibia, as described further herein.

After both the proximal anchor element 142 is fixed in operation 516 to the tibia (and after the distal anchor element is fixed in operation 510 to the calcaneus), the physician may begin the process of transferring in operation 518 a compressive load of the intramedullary medical device 114 to the ankle joint (e.g., tibia 102, talus 106, and calcaneus 108) of the patient. For example, with the intramedullary medical device 114 attached to the bones of the patient through both the distal and the proximal anchor elements, and the bones of the patient's ankle in position to receive the compressive load of the intramedullary medical device, the physician may transfer in operation 518 the compressive load being held between the proximal structure 300 and the compression 200 structure of the installation assembly 100 to the ankle joint of the patient.

In one embodiment, before the compressive load is transferred in operation 518, the compression structure 200 of the installation assembly may be fixed to the distal anchor element of the intramedullary medical device and the proximal structure may be fixed to a rigid element of the intramedullary medical device which is attached to a proximal anchor element 142. Therefore, compressive forces of the intramedullary medical device 114 between the distal anchor element and the proximal anchor element 142 may be held between the proximal structure 300 and the compression structure 200 of the installation assembly 100. The installation assembly 100 holds this compressive load while the intramedullary medical device is being fixed to the bones of the patient.

In one embodiment, the installation assembly 100 may controllably transfer in operation 518 this compressive load to the bones of the patient through reducing the compressive load held between the compression structure 200 and the proximal structure 300 of the installation assembly 100, as described further herein. For example, the compression structure 200 may be manipulated by the physician to allow the distal anchor element to move proximally along the long access of the intramedullary medical device, thereby compressing the ankle joint of the patient under the load of the compression element of the intramedullary medical device 114. If the ankle joint of the patient has already been compressed as in operation 514 by the physician (e.g., using a slideable interconnection of the installation assembly 100), the proximal movement of the distal anchor element while the compressive load is transferred in operation 518 may be small (e.g., relative to the inter joint site compression). For example, the proximal movement in the distal anchor element (e.g., through release of strain in the compressive element of the intramedullary medical device) may correspond to a strain increase in the ankle joint related to the increased compressive load transferred in operation 518 to the ankle joint.

In one embodiment, after the compressive load is transferred in operation 518 to the ankle joint, the supra-proximal structure is unfixed in operation 520 from the patient's tibia 102. As described further herein, the ankle joint may compress (e.g., be strained) further under the new load supplied by intramedullary medical device 114. The supra-proximal structure may be unfixed 520 after this compressive load has been supplied (e.g., through transfer operation 518) by the intramedullary medical device.

In another embodiment, the supra-proximal structure may be unfixed in operation 520 before the compressive load of the intramedullary medical device is transferred 518 to the ankle joint of the patient. In this embodiment, the ankle joint of the patient is first compressed in operation 514 between the supra-proximal structure 400 and the proximal structure 300 of the installation assembly through the slideable interface between these two structures that is controlled by the physician. Then the proximal anchor element 142 is fixed in operation 516 to the tibia 102, thereby holding the same ankle joint compression between the distal structure 200 and the supra-proximal structure 400 that was first established between the proximal structure 300 and the supra-proximal structure 400. Thereafter, the supra-proximal structure 400 of the installation assembly may be unfixed in operation 520 from the patient's tibia 102. The compressive load of the intramedullary medical device may be thereafter transferred in operation 518 to the ankle joint thereby further compressing the ankle joint under the load determined by the compression element of the intramedullary medical device 114. The transferring 518 of the load to the ankle joint may be performed as described further herein through releasing the relative distance between the compression structure and the proximal structure of the installation assembly.

After transferring the load in operation 518 to the ankle joint of the patient and unfixing 520 the supra-proximal structure, the proximal structure and the compression structure of the installation assembly may be removed from the intramedullary medical device, and the installation assembly may be removed 522 from the patient. For example, if a cross support 406 is provided between the supra-proximal structure drill guide ports of the installation assembly 100, the cross support may be removed or detached from the supra-proximal structure drill guide supports and the rest of the installation assembly may be slid distally with respect to the patient or lifted away from the patient in order to remove 522 the installation assembly away from the patient.

What is claimed is:

1. An installation assembly for installing an intramedullary medical device into a patient, the installation assembly comprising:
   a proximal drill guide holder registered to a proximal anchor element of an intramedullary medical device;
   a distal drill guide holder registered to a distal anchor element of the intramedullary medical device;
   a distal anchor element lock attached to the distal drill guide holder and adapted to connect with the distal anchor element;
   a first compression assembly connecting the distal drill guide holder and the proximal drill guide holder and adapted to translate distally both the distal drill guide holder and the distal anchor element lock with respect to the proximal drill guide holder;
   a supra-proximal drill guide holder registered to a supra-proximal position located proximally relative to the proximal anchor element;
   a second compression assembly connecting the supra-proximal drill guide holder and the proximal drill guide holder and adapted to translate the proximal drill guide holder proximally with respect to the supra-proximal anchor drill guide holder.

2. The intramedullary medical device installation assembly of claim 1, wherein the distal drill guide holder comprises a first tube disposed within the proximal drill guide holder that comprises a second tube disposed within the supra-proximal drill guide holder that comprises a third tube.

3. The intramedullary medical device installation assembly of claim 2, wherein the first tube, the second tube, and the third tube are slideably interconnected.

4. The intramedullary medical device installation assembly of claim 1, wherein the proximal drill guide holder is attached to an intramedullary medical device pedestal adapted to connect with a rigid element of the intramedullary medical device that is connected to the proximal anchor element.

5. The intramedullary medical device installation assembly of claim 4, wherein the intramedullary medical device pedestal is further adapted to connect with the rigid element in a single rotational configuration with respect to an axis of the intramedullary medical device.

6. The intramedullary medical device installation assembly of claim 4, wherein the intramedullary medical device pedestal is further adapted to hold the rigid element in a stationary position within the patient while both the distal anchor element and the distal drill guide holder are translated distally.

7. An installation assembly for installing an intramedullary medical device into a patient, the installation assembly comprising:
   a distal drill guide holder carriage connecting a first distal drill guide holder to a second distal drill guide holder, wherein the distal drill guide holder carriage is further connected to a distal anchor element lock adapted to attach the distal drill guide holder carriage to a distal anchor element of an intramedullary medical device having a central axis;
   wherein the distal drill guide holder carriage is further adapted to translate both the first and second distal drill guide holders parallel to the central axis of the intramedullary medical device and registered to a first position along the central axis that includes the distal anchor element;
   a proximal drill guide holder carriage connecting a first proximal drill guide holder to a second proximal drill guide holder, the proximal drill guide holder carriage slideably connected with the distal drill guide holder carriage through a compression assembly adapted to translate the distal anchor element lock along the central axis, from an initial position with respect to a proximal anchor element of the intramedullary medical device;
   wherein the proximal drill guide holder carriage is further adapted to translate both the first and second proximal drill guide holders parallel to the central axis of the intramedullary medical device and registered to a second position along the central axis that includes the proximal anchor element;
   an initial compression stop of the compression assembly adapted to limit the compression assembly from distally translating the distal anchor element lock past a predetermined maximum compression distance along the central axis from the initial position;
   a strain release stop adapted to limit the compression assembly, once the distal anchor element has been distally translated at least to a predetermined minimum installed distance, from proximally translating the distal anchor element to less than a selectable installed distance;
   a supra-proximal drill guide holder carriage connecting a first supra-proximal drill guide holder to a second supra-proximal drill guide holder, the supra-proximal drill guide holder carriage slideably connected with the proximal drill guide holder carriage through a joint-compression assembly adapted to translate the proximal drill guide holder carriage with respect to the supra-proximal drill guide holder carriage; and wherein the supra-proximal drill guide holder carriage is further adapted to translate the first and second supra-proximal drill guide holders parallel to the central axis of the intramedullary medical device and registered to a third supra-proximal position located proximally with respect to the proximal anchor element.

8. A planar telescoping intramedullary medical device installation assembly comprising:

an intramedullary medical device interface adapted to hold an intramedullary medical device having a central axis within the intramedullary medical device installation assembly;

a first telescoping assembly with a first distal drill guide holder, a first proximal drill guide holder, and a first supra-proximal drill guide holder each of which is adapted to hold a drill guide in a drill plane that includes the central axis;

a second telescoping assembly with a second distal drill guide holder, a second proximal drill guide holder, and a second supra-proximal drill guide holder each of which is adapted to hold a drill guide in the drill plane;

a distal drill guide holder carriage adapted to hold the first distal drill guide holder to the second distal drill guide holder in the drill plane and in a distal registered position relative to a distal anchor element of an intramedullary medical device;

a proximal drill guide holder carriage adapted to hold the first proximal drill guide holder to the second proximal drill guide holder in the drill plane and in a registered position relative to a proximal anchor element of the intramedullary medical device;

a supra-proximal drill guide holder carriage adapted to hold the first supra-proximal drill guide holder to the second supra-proximal drill guide holder in the drill plane and in a registered position relative to a proximal anchor element of the intramedullary medical device;

wherein the first distal drill guide holder and the second distal drill guide holder share a distal axis that is perpendicular to the central axis;

wherein the first proximal drill guide holder and the second proximal drill guide holder share a proximal axis that is perpendicular to the central axis; and wherein the first supra-proximal drill guide holder and the second supra-proximal drill guide holder share a supra-proximal axis that is perpendicular to the central axis.

9. The intramedullary medical device installation assembly of claim 8, wherein the first and second telescoping assemblies lie in the drill plane and are parallel to the central axis.

10. The intramedullary medical device installation assembly of claim 8, wherein the first telescoping assembly includes:

a first distal sheath comprising the first distal drill guide holder;

a first proximal sheath comprising the first proximal drill guide holder, wherein first distal sheath is disposed within the first proximal sheath and the first proximal sheath comprises a first distal access port adapted to provide access to the first distal drill guide holder; and a first supra-proximal sheath comprising the first supra-proximal drill guide holder, wherein the first proximal sheath is disposed within the first supra-proximal sheath and the first supra-proximal sheath comprises a first proximal access port adapted to provide access to the first proximal drill guide holder.

11. The intramedullary medical device installation assembly of claim 10, wherein the second telescoping assembly includes:

a second distal sheath comprising the second distal drill guide holder;

a second proximal sheath comprising the second proximal drill guide holder, wherein second distal sheath is disposed within the second proximal sheath and the second proximal sheath comprises a second distal access port adapted to provide access to the second distal drill guide holder; and a second supra-proximal sheath comprising the second supra-proximal drill guide holder, wherein the second proximal sheath is disposed within the second supra-proximal sheath and the second supra-proximal sheath comprises a second proximal access port adapted to provide access to the second proximal drill guide holder.

12. The intramedullary medical device installation assembly of claim 10, wherein the first distal access port is adapted to disallow access to the first distal drill guide holder in a range of strains of a contracting element of the intramedullary medical device between a maximum strain distance of the contracting element and a maximum installed strain distance of the contracting element.

13. The intramedullary medical device installation assembly of claim 7, wherein the first compression assembly comprises a lever assembly movably connecting the proximal drill guide holder and the distal drill guide holder.

14. The intramedullary medical device installation assembly of claim 7, further comprising:

an access port for the first proximal drill guide holder adapted only to allow access to the first proximal drill guide in configurations of the intramedullary medical device installation assembly whereby the distal anchor element is less than a predetermined maximum installed compression distance that is less than the predetermined maximum compression distance.

15. The intramedullary medical device installation assembly of claim 14, wherein the initial compression stop is further adapted such that the predetermined maximum compression distance is about 2 millimeters greater than the predetermined maximum installed compression distance.

16. The intramedullary medical device installation assembly of claim 7, wherein the first distal drill guide holder comprises a first tube disposed within the first proximal drill guide holder that comprises a second tube disposed within the first supra-proximal drill guide holder that comprises a third tube.

17. The intramedullary medical device installation assembly of claim 16, wherein the first tube, the second tube, and the third tube are slideably interconnected.

18. The intramedullary medical device installation assembly of claim 7, further comprising:

a detachable supra-proximal brace at least partially disposed at the supra-proximal position.

19. The intramedullary medical device installation assembly of claim 7, wherein the proximal drill guide holder carriage is attached to an intramedullary medical device pedestal adapted to connect with a rigid element of the intramedullary medical device that is connected to the proximal anchor element.

20. The intramedullary medical device installation assembly of claim 19, wherein the intramedullary medical device pedestal is further adapted to connect with the rigid element in a single rotational configuration with respect to the central axis.

21. The intramedullary medical device installation assembly of claim 19, wherein the intramedullary medical device pedestal is further adapted to hold the rigid element in a stationary position within the patient while both the distal anchor element and the distal drill guide holder carriage are translated distally.

22. The intramedullary medical device installation assembly of claim 7, wherein the compression assembly comprises a lever assembly disposed between the proximal drill guide holder carriage and the distal drill guide holder carriage.

\* \* \* \* \*